(12) United States Patent
Aliamiri et al.

(10) Patent No.: US 11,147,463 B2
(45) Date of Patent: Oct. 19, 2021

(54) METHOD AND APPARATUS FOR HIGH ACCURACY PHOTOPLETHYSMOGRAM BASED ATRIAL FIBRILLATION DETECTION USING WEARABLE DEVICE

(71) Applicant: Samsung Electronics Co., Ltd., Suwon-si (KR)

(72) Inventors: Alireza Aliamiri, San Jose, CA (US); Yichen Shen, Santa Clara, CA (US)

(73) Assignee: Samsung Electronics Co., Ltd.

( * ) Notice: Subject to any disclaimer, the term of this patent is extended or adjusted under 35 U.S.C. 154(b) by 495 days.

(21) Appl. No.: 15/885,581

(22) Filed: Jan. 31, 2018

(65) Prior Publication Data

US 2019/0133468 A1 May 9, 2019

Related U.S. Application Data

(60) Provisional application No. 62/581,569, filed on Nov. 3, 2017.

(51) Int. Cl.

| *A61B 5/024* | (2006.01) |
|---|---|
| *A61B 5/00* | (2006.01) |
| *A61B 5/0205* | (2006.01) |
| *A61B 5/361* | (2021.01) |

(52) U.S. Cl.
CPC ........ *A61B 5/02416* (2013.01); *A61B 5/7221* (2013.01); *A61B 5/7275* (2013.01); *A61B 5/0205* (2013.01); *A61B 5/02438* (2013.01); *A61B 5/361* (2021.01); *A61B 5/721* (2013.01); *A61B 5/7225* (2013.01); *A61B 5/7267* (2013.01)

(58) Field of Classification Search
CPC ..... A61B 5/721; A61B 5/7221; A61B 5/7225; A61B 5/7275
See application file for complete search history.

(56) References Cited

U.S. PATENT DOCUMENTS

| 7,689,833 B2 | 3/2010 | Lange |
| 8,862,214 B2 | 10/2014 | Ghodrati |
| 2014/0330134 A1 | 11/2014 | Chon et al. |
| 2015/0164349 A1* | 6/2015 | Gopalakrishnan ..... G16H 20/40 600/508 |

(Continued)

OTHER PUBLICATIONS

Alireza Aliamiri and Yichen Shen, "Deep Learning Based Atrial Fibrillation Detection Using Wearable Photoplethysmography Sensor," submitted to 2018 IEEE International Conference on Biomedical and Health Informatics on Nov. 6, 2017.

*Primary Examiner* — Puya Agahi
(74) *Attorney, Agent, or Firm* — Innovation Counsel LLP

(57) ABSTRACT

An apparatus includes a sensor module, a data processing module, a quality assessment module and an event prediction module. The sensor module provides biosignal data samples and motion data samples. The data processing module processes the biosignal data samples to remove baseline and processes the motion data samples to generate a motion significant measure. The quality assessment module generates a signal quality indicator based on the processed biosignal data sample segments and the corresponding motion significance measure using a first deep learning model. The event prediction module generates an event prediction result based on the processed biosignal data sample segments associated with a desired signal quality indicator using a second deep learning model.

14 Claims, 8 Drawing Sheets

(56) References Cited

U.S. PATENT DOCUMENTS

| | | | |
|---|---|---|---|
| 2015/0265217 A1* | 9/2015 | Penders | A61B 5/721 600/301 |
| 2016/0135706 A1 | 5/2016 | Sullivan et al. | |
| 2017/0032221 A1 | 2/2017 | Wu et al. | |
| 2017/0143266 A1 | 5/2017 | Kovacs et al. | |
| 2018/0140203 A1* | 5/2018 | Wang | A61B 5/0205 |

* cited by examiner

User-Wearable Device
100

Back View

Front View

METHOD AND APPARATUS FOR HIGH ACCURACY PHOTOPLETHYSMOGRAM BASED ATRIAL FIBRILLATION DETECTION USING WEARABLE DEVICE

CROSS REFERENCE TO RELATED APPLICATIONS

This application claims priority to U.S. Provisional Patent Application No. 62/581,569, entitled METHOD AND APPARATUS FOR HIGH ACCURACY PHOTOPLETHYSMOGRAM BASED ATRIAL FIBRILLATION DETECTION USING WEARABLE DEVICE, filed Nov. 3, 2017, which is incorporated herein by reference for all purposes.

FIELD

The present disclosure relates to a medical monitoring device and method thereof, and, in particular, to a system and method for atrial fibrillation detection using a wearable device.

BACKGROUND

Atrial Fibrillation (AFib) is one of the most common cardiac arrhythmia, with prevalence of approximately 2% of the general population in the developed world. The presence of AFib could potentially lead to major health risks. Traditionally, AFib is detected by an electrocardiogram (ECG). While ECG based approach achieves very high accuracy in AFib detection, monitoring ECG signal requires sophisticated devices that have multiple electrodes installed and the process requires active human participation. Recently, photoplethysmography (PPG) has become a promising alternative to ECG in AFib detection. The advantage of PPG-based solution is that PPG signals can be easily recorded and monitored from consumer-level wearable devices with no active effort from participants. This advantage, together with affordable wearable devices and smart phones, can make daily-basis, user friendly AFib monitoring and detection available to general public, which may lead to huge beneficial impact on AFib-affected population.

Utilizing PPG signals collected from wearable devices is challenging due to various types of noise affecting the signal quality. The signal quality can be drastically affected by the quality of sensors and motion from users. The artifact noise from both sensors and user movements can mask any signals useful for detecting AFib. Previous studies on PPG signals collected from wearable devices tried to tackle this problem by using handcrafted signal quality index calculated by PPG data or accelerometer data. However, in reality, these manually engineered features are likely to suffer from high bias and poor generalizability. The unfiltered low quality signal will likely deteriorate the performance in AFib detection in real use cases.

SUMMARY

The present disclosure discloses a device and method for atrial fibrillation detection substantially as shown in and/or described below, for example in connection with at least one of the figures, as set forth more completely in the claims.

These and other advantages, aspects and novel features of the present disclosure, as well as details of an illustrated embodiment thereof, will be more fully understood from the following description and drawings.

In one embodiment, an apparatus includes a sensor module including a first sensor configured to measure a biological signal and a second sensor configured to measure a motion signal where the sensor module provides biosignal data samples and motion data samples as output; a data processing module configured to process segments of the biosignal data samples where each segment includes biosignal data samples collected over a predetermined time duration. The data processing module is configured to remove a signal baseline from each segment of biosignal data samples and to generate processed biosignal data sample segments, and is further configured to generate a motion significance measure for each segment of biosignal data samples using the motion data samples collected contemporaneously with the biosignal data samples, the motion significance measure being indicative of a degree of motion during the sensing of the respective segment of biosignal data samples. The apparatus further includes a quality assessment module configured to generate a signal quality indicator based on the processed biosignal data sample segments and the corresponding motion significance measure using a first deep learning model; and an event prediction module configured to generate an event prediction result based on the processed biosignal data sample segments associated with a desired signal quality indicator using a second deep learning model.

BRIEF DESCRIPTION OF THE DRAWINGS

Various embodiments of present disclosure are disclosed in the following detailed description and the accompanying drawings.

DETAILED DESCRIPTION

Figure 1A:
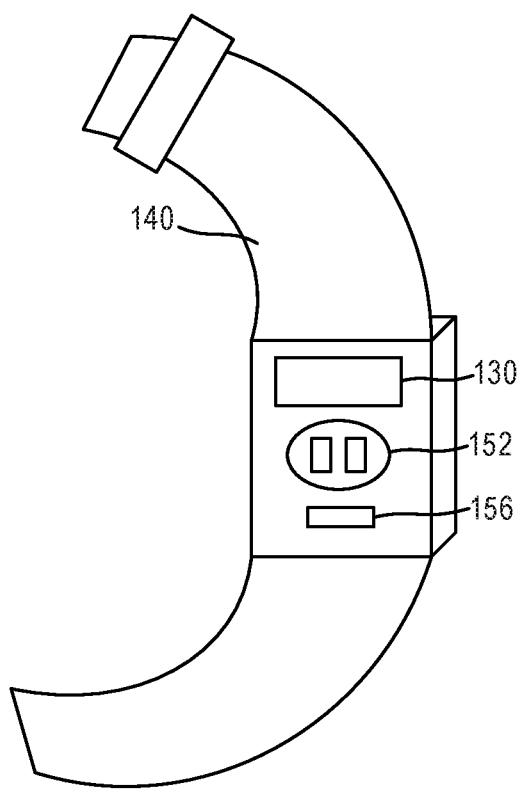
FIG. 1 illustrates an electronic device according to embodiments of the present invention.

Present disclosure can be implemented in numerous ways, including as a process; an apparatus; a system; a composition of matter; a computer program product embodied on a computer readable storage medium; and/or a processor, such as a hardware processor or a processor device configured to execute instructions stored on and/or provided by a memory coupled to the processor. In this specification, these implementations, or any other form that present disclosure may take, may be referred to as techniques. In general, the order of the steps of disclosed processes may be altered within the scope of present disclosure. Unless stated otherwise, a component such as a processor or a memory described as being configured to perform a task may be implemented as a general component that is temporarily configured to perform the task at a given time or a specific component that is manufactured to perform the task. As used herein, the term 'processor' refers to one or more devices, circuits, and/or processing cores configured to process data, such as computer program instructions.

A detailed description of one or more embodiments of present disclosure is provided below along with accompanying figures that illustrate the principles of present disclosure. Present disclosure is described in connection with such embodiments, but present disclosure is not limited to any embodiment. The scope of present disclosure is limited only by the claims and present disclosure encompasses numerous alternatives, modifications and equivalents. Numerous specific details are set forth in the following description in order to provide a thorough understanding of present disclosure. These details are provided for the purpose of example and present disclosure may be practiced according to the claims without some or all of these specific details. For the purpose of clarity, technical material that is known in the technical fields related to present disclosure has not been described in detail so that present disclosure is not unnecessarily obscured.

In embodiments of the present invention, a user-wearable device implements an atrial fibrillation (AFib) detection system to provide high accuracy AFib detection using a channel of a biological sensor signal and a motion signal and using only the computational power provided by the wearable device. In some embodiments, the wearable device includes a biophysiological sensor and an inertial measurement sensor to collect biological signal and motion signal of a subject wearing the user-wearable device. The user-wearable device further implements a neural network utilizing deep learning models to detect AFib using the biological signal and the motion signal. In some embodiments, the biophysiological sensor is a photoplethysmography (PPG) sensor and the inertial measurement sensor is an accelerometer. In this manner, the user-wearable device realizes a portable, non-intrusive and low-cost solution for AFib monitoring and detection which can be made accessible to the general population. In other embodiments, the user-wearable device can be adapted as a medical monitoring device for detecting other biological sensor signals and using the detected biological sensor signal with the subject's motion data to detect a medical event of interest. The configuration and application of the user-wearable device of the present disclosure is not limited to AFib detection only and can have wide applications in health monitoring.

The user-wearable device for AFib detection of the present invention realizes many advantages over conventional systems and methods. First, the AFib detection system of the present invention uses a single channel of biological signal and a single channel of motion signal and a light-weight AFib detection method that directly applies deep neural networks on raw signals from the sensors with minimum preprocessing or transformation. Accordingly, the AFib detection system can be effectively implemented in a wearable device while providing highly accurate AFib detection. Second, the AFib detection system evaluates the biological signal with the motion signal using a deep learning model to assess the quality of the biological signal, without manually constructing quality measurements. In this manner, only biological signal with a good signal quality is used for AFib detection, thus ensuring robust AFib prediction results.

In one embodiment, the AFib detection system includes a quality assessment network implemented by training an auxiliary convolutional neural network (CNN) using raw biological sensor signal as input to accurately assess the quality of signals collected from the biophysiological sensor, without manually constructing quality measurements. The quality assessment network acts as a gate keeper and identifies segments of raw biological sensor signal with good signal quality and hence are suitable for AFib detection. The AFib detection system further includes an AFib prediction network being another trained CNN that predicts the probability of AFib presence in the signals provided by the quality assessment network. The AFib detection system of the present invention achieves high accuracy in AFib detection comparable to state-of-art ECG based approaches, yet having a simple structure that can be implemented in a small mobile device such as a wrist-band wearable device.

Figure 1B:
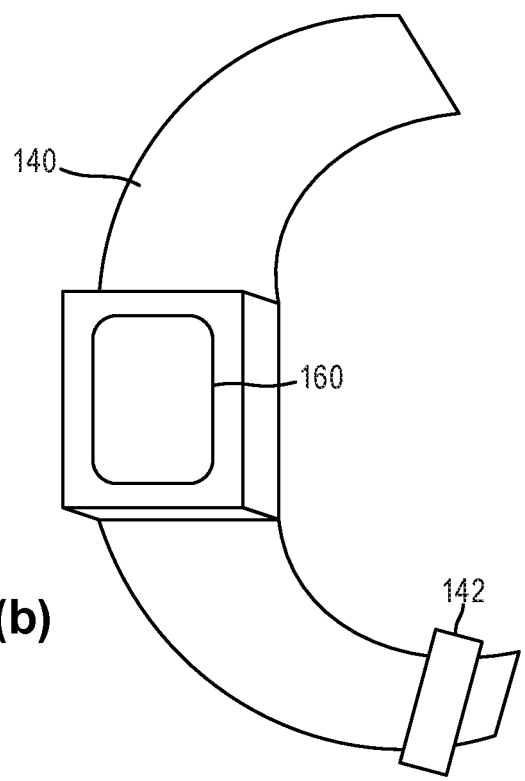

FIG. 1 illustrates an electronic device according to embodiments of the present invention. Referring to FIG. 1, an electronic device 100, which may be a user-wearable device, has a display 160, a processor 130, a sensor module 150, a battery (not show), a band 140, and a clasp 142. The band 140 may be wrapped around a wrist and the user-wearable device 100 may be held on the wrist by using the clasp 142. The sensor module 150 include one or more sensors 152, 154 and a local processor 154. The local processor 154 implements control function for the sensor module and may also perform processing or pre-processing of the sensed signals. The processor 130 implements control functions for the user-wearable device and may also perform further signal processing functions on the sensed signals. The local processor 154 or the processor 130 may also be referred to as a diagnostic processor.

Although the user-wearable device 100 may be worn on a wrist, various embodiments of the disclosure need not be so limited. The user-wearable device 100 may also be designed to be worn on other parts of the body, such as, for example, on an arm (around the forearm, the elbow, or the upper arm), on a leg, on the chest, on the head like a headband, on the throat like a "choker," and on an ear. The user-wearable device 100 may be able to communicate with other electronic devices such as, for example, a smart phone, a laptop, or various medical devices at a hospital or a doctor's office.

The display 160 may output monitored physiological signals from the user's body for viewing by the user and/or others. The physiological signals being monitored are sometimes referred to as biosignals or biometric data. The monitored biosignals may be, for example, heart (pulse) rate, pulse morphology (shape), pulse spacing (inter-beat intervals), respiration (breathing) rate, and blood pressure. The display 160 may also output instructions to the user or others in the use of the user-wearable device 100 or use of other measurement devices, as well as status and diagnostic results, for example.

The processor 130 receives the monitored or sensed signals from sensors in the sensor module 150. For example, the sensors 152, 156 acquire signals from the user's wrist when the user-wearable device 100 is worn by a user. In embodiments of the present invention, the sensor module 150 includes a sensor 152 being a biophysiological sensor and a second sensor 156 being an inertial measurement sensor. In one embodiment, the biophysiological sensor is a photoplethysmography (PPG) sensor and the inertial measurement sensor is an accelerometer. The sensor module 150 may include the processor 154 for controlling the sensors 152, 156, and also for processing the signals sensed by the sensors. For example, the processor 154 may decompose the signals monitored by the sensors 152, 156, and then reconstruct the decomposed signals. Various embodiments of the disclosure may have the processor 130 also performing the functions of the processor 154. Various embodiments of the disclosure may also have different number of sensors.

In some embodiments, the sensor 152 is a PPG sensor used to continuously or periodically monitor cardio-related physiological information, such as heart pulse rate or heart pulse shape, of a user. Meanwhile, the sensor 156 is an accelerometer used to continuously or periodically monitor motion information of a user. The sensor module 150 may include other sensors such as, for example, a thermometer for taking the user's temperature.

The user-wearable device 100 implements the AFib detection system of the present invention in the processor 130. The AFib detection system includes a quality assessment network for evaluating the quality of the biophysiological signal measured by the biophysiological sensor 152 using the motion signal measured by the inertial measurement sensor 154, and further includes an AFib prediction network for evaluating the biophysiological signal that are determined to be of good quality and estimating the probability of the presence of AFib in the monitored signal. The detail structure of the AFib detection system will be described in more detail below.

Figure 2:
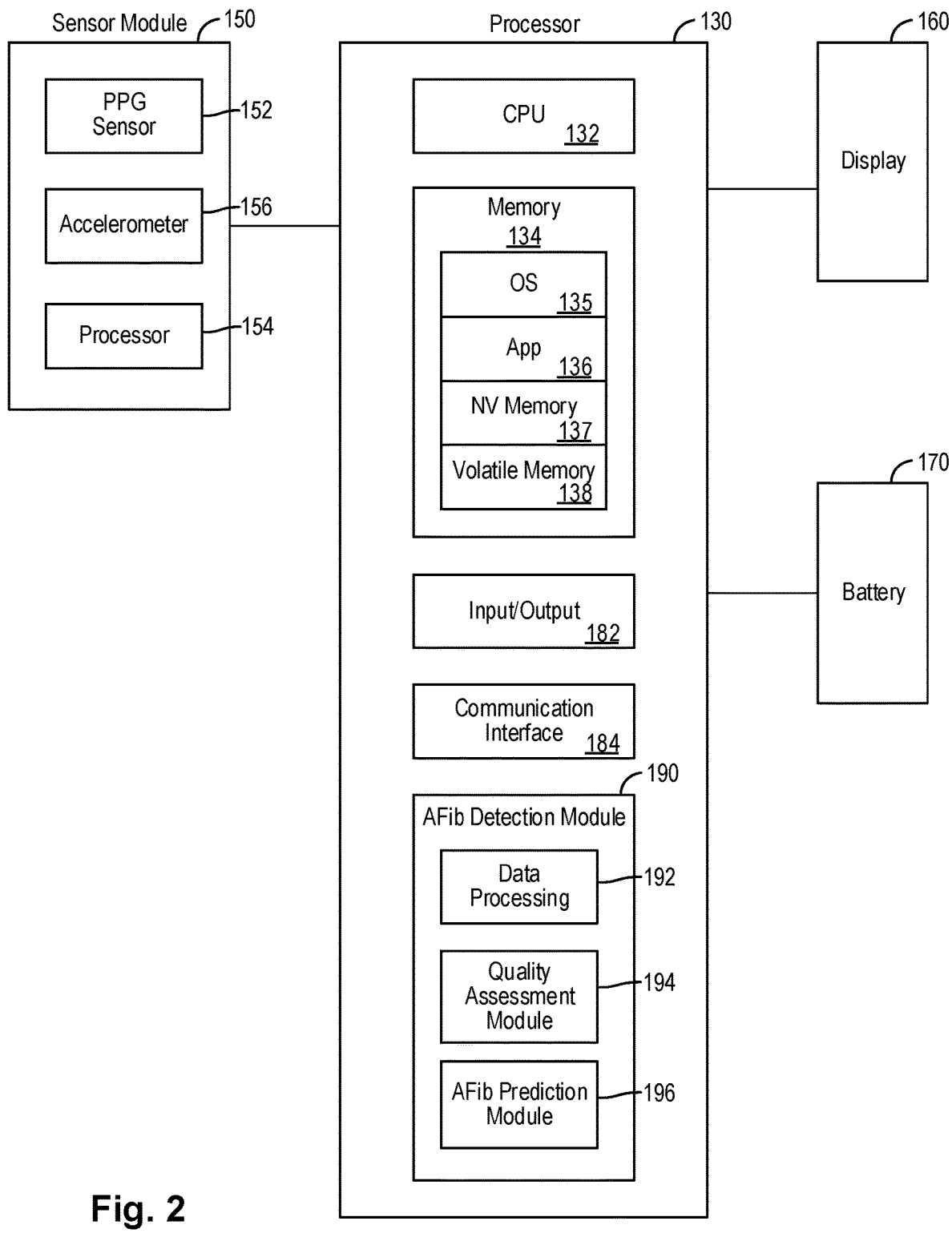
FIG. 2 illustrates a block diagram of an electronic device according to embodiments of the present invention.

FIG. 2 illustrates a block diagram of an electronic device according to embodiments of the present invention. Referring to FIG. 2, a user-wearable device 100 includes a sensor module 150, a processor 130, a display 160 and a battery 170 for providing power to the other components. The processor 130 controls the output provided on the display 160. The display 180 may also include input devices (not shown) such as, for example, buttons, dials, touch sensitive screen, and microphone.

In embodiments of the present invention, the sensor module 150 includes at least one biophysiological sensor 152 to measure a biological signal of the user. In the present embodiment, the biophysiological sensor 152 is a PPG sensor. The sensor module 150 further includes at least one inertial measurement sensor 156 to measure a motion signal of the user. In the present embodiment, the inertial measurement sensor 156 is an accelerometer, such as a tri-axial accelerometer. The sensor module 150 may be provided with a local processor 154 for controlling the sensors 152, 156, and also for processing the biosignals and motion signals sensed by the sensors 152, 156 respectively. In some embodiments, the signal processing operation can be implemented at the local processor 154 and/or at the processor 130. Alternately, the local processor 154 may perform part of the signal processing, such as certain signal pre-processing, and the processor 130 implements other signal processing algorithms for biometric determination or other functions. In embodiments of the present invention, the specific processor used to execute the biometric signal processing algorithms is not critical to the practice of the present invention.

In embodiments of the present invention, the processor 130 is configured for controlling the sensing operation, the sampling schedule, the signal processing operation, and device communication events and other device-specific functions in the user-wearable device. In the present embodiment, the processor 130 include a CPU 132, memory 134, an input/output (I/O) interface 182, a communication interface 184, and an AFib detection module 190. While the processor 130 is described as comprising these various devices, other embodiments may use other architectures where the different functionalities are grouped differently. For example, the grouping may be in different integrated circuit chips. Or the grouping may be combining different devices such as the I/O interface 182 and the communication interface 184 together.

The processor 130 incorporates the AFib detection module 190 to perform AFib detection on the sensed biosignal, such as the PPG signal, using the motion signal, such as the motion signal from the accelerometer. In embodiments of the present invention, the AFib detection module includes a data processing module 192, a quality assessment module 194 and an AFib detection module 196. The signal processing module 192 is configured to perform signal preprocessing on the sensed biosignal. For example, the data processing module may perform baseline removal or DC signal level removal on the sensed biosignals. The quality assessment module implements a quality assessment network which acts as a gate keeper and identifies segments of raw PPG signal with good quality and is therefore suitable for AFib detection. The AFib detection module implements an AFib prediction network which predicts the probability of AFib presence in the good quality signals provided from the quality assessment network.

Figure 3:
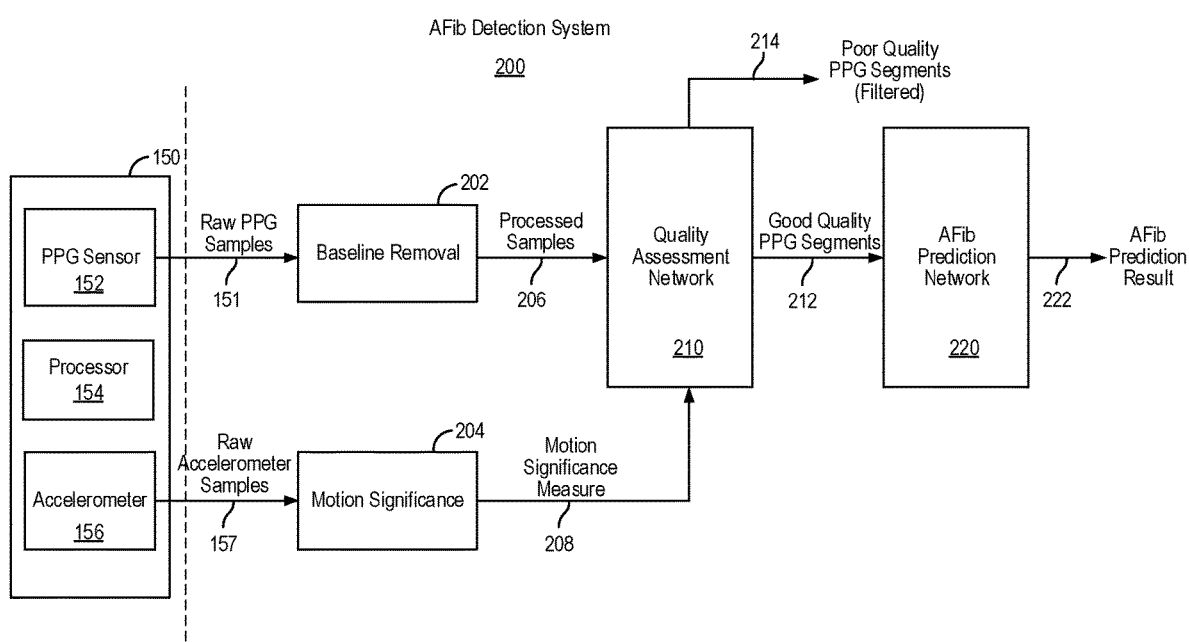
FIG. 3 illustrates the AFib detection system in embodiments of the present invention.

FIG. 3 illustrates the AFib detection system in embodiments of the present invention. In some embodiments, the AFib detection system of FIG. 3 is implemented as the AFib detection module 190 in the processor 130 of the wearable device 100. Referring to FIG. 3, the AFib detection system 200 is in communication with a sensor module 150 to receive sensed biological signal and motion signal. In the present example, the sensor module 150 includes a PPG sensor 152 providing a PPG signal as the biological signal and an accelerometer 156 providing accelerometer signal as the motion signal. The sensor module may include a local processor 154 to provide certain signal pre-processing and control functions. It is understood that the biological signal and the motion signal are both time-series signals and are usually continually measured in electrical voltage levels at a given sampling rate. Accordingly, in operation, a biological signal measured by a biophysiological sensor is provided as a time-series of biosignal data samples. Similarly, a motion signal measured by an inertial measurement sensor is provided as motion data samples. In the present example, both the PPG sensor and the accelerometer are operating at a sampling rate of 100 Hz, that is, 100 samples per second.

In the present example, the PPG sensor 152 provides raw PPG data samples (node 151) as output while the accelerometer 156 provides raw accelerometer data samples (node 157) as output. In the present description, a "raw" signal refers to a sensed signal which has not be processed or has only been minimally processed.

In the present description, the biological signal being monitored is referred to as the PPG signal, but it is understood that other types of biological signal may be used in the AFib detection system of the present invention. The use of the PPG sensor is illustrative only and is not intended to be limiting. In other embodiments, the biological signal can be any other cardio-related physiological signal. Moreover, in the following description, the motion signal is measured by an accelerometer, but it is understood that other types of motion sensor or inertial measurement sensor may be used to obtain the motion signal. The use of the accelerometer is illustrative only and not intended to be limiting.

The AFib detection system 200 receives the raw PPG data samples and the raw accelerometer samples. A salient feature of the AFib detection system 200 of the present invention is that the AFib detection system uses only a single channel of the PPG data samples and a single channel of the accelerometer samples to provide highly accurate AFib prediction results. Accordingly, the AFib detection system can be implemented using a small computational structure, making it suitable for implementation in a wearable device.

In the AFib detection system 200, the raw PPG data samples are provided to a baseline removal module 202 to remove a baseline signal level or a DC offset from the signal. For example, the baseline signal level is removed so that the PPG data samples have voltage values that are centered at approximately zero volt. In some embodiments, the raw PPG data samples are processed as segments of PPG data samples where each segment includes PPG data samples collected over a given time duration, for example, 30 seconds. At a sampling rate of 100 Hz, each segment contains 3000 PPG data samples. The baseline removal module 202 operates on segments of PPG data samples and generates processed PPG data sample segments as output.

Meanwhile, the raw accelerometer data samples are provided to a motion significance module 204 for evaluation. For each segment of PPG data samples, there is a corresponding segment of motion data samples that are collected contemporaneously with the PPG data samples. The motion significance module 204 generate a motion significance measure for each segment of PPG data samples using the corresponding motion data samples. In particular, the motion significance measure is indicative of a degree of motion during the sensing of the respective segment of PPG data samples. In one embodiment, the motion significance measure includes a first motion indicator indicating moderate motion and a second motion indicator indicating vigorous motion. The motion significance module 204 evaluates the motion data samples and classifies the motion data samples corresponding to a respective segment of PPG data samples using the first motion indicator or the second motion indicator. In one embodiment, the raw motion data samples are processed in segments, in the same manner as the raw PPG data samples. In one embodiment, the motion significance module 204 generates the motion significance measure (node 208) for each segment of motion data samples based on an average of magnitudes in three axes of the motion signal sensed by the accelerometer.

The AFib detection system 200 includes the quality assessment network 210 which receives the processed PPG data sample segments and the corresponding motion significance measure. The quality assessment network 210 evaluates the processed biosignal data sample segment with the motion significance measure using a first deep learning model that was previously trained based on a set of quality labels and one or more sets of quality training data. In operation, the quality assessment network 210 generating a signal quality indicator as output where the signal quality indicator identifies each processed biosignal data sample segment as having good signal quality or poor signal quality. In practice, the quality assessment network 210 filters out PPG data sample segments with poor signal quality (node 214) and only allow the good signal quality PPG data sample segments (212) to move to the next stage for AFib prediction. Because only PPG data sample segments with good quality is used in AFib prediction, the AFib detection system 200 is capable of making robust and reliable AFib predictions.

A salient feature of the quality assessment network 210 is the use of the motion significant measure (node 208) in evaluating the signal quality of the PPG data samples. The motion data samples are not used merely to set a threshold for good versus bad signal quality. Rather, the motion data is used in conjunction with the morphology of the PPG data samples and applied to the first deep learning model to classify the quality of the PPG data samples. For instance, in some cases, even if the motion is vigorous, the signal quality can still be good. Alternately, in some cases, even if there is the motion moderate, the signal quality may be bad. The first deep learning model classify the quality of the PPG data samples in view of the motion data to providing meaningful quality assessment results. The structure of the quality assessment network 210 will be described in more detail below.

The AFib detection system 200 includes the AFib prediction network 220 which receives the processed PPG data sample segments provided by the quality assessment network 210. That is, the AFib prediction network 220 receives only processed PPG data sample segments which have been evaluated to have good signal quality. The AFib prediction network 220 evaluates the processed biosignal data sample segments using a second deep learning model that was previously trained based on AFib annotations and one or more sets of AFib detection training data. The AFib prediction network is configured to generate a prediction result (node 222) indicative of a probability that atrial fibrillation is present in a given segment of the biosignal data samples. In response to AFib being detected to be present in certain segment of the biosignal data samples, the AFib detection system 200 may sends a notification to the user. For example, the notification may be sent via an application on a mobile device and/or the wearable device.

In an alternate embodiment, the AFib prediction network 220 also receives the motion significance measure and the good quality PPG data same segment, with the associated motion significance measure, are then evaluated using the second deep learning model.

In one embodiment, the first deep learning model implemented in the quality assessment network 210 is a multi-modal neural network including three convolutional layer with max-pooling, batch normalization and rectified linear unit as activation function, followed by one fully-connected layer and one output layer, wherein the output from the convolutional layers are flattened and concatenated with the motion significance measure for that processed biosignal data sample segment and is fed into the fully connected layer.

In another embodiment, the second deep learning model implemented in the AFib prediction network 220 is a hybrid model of convolutional neural network (CNN) and recurrent neural network (RNN), wherein each segment of processed biosignal data samples is split into a plurality of sub-segments where each sub-segment is fed into gated recurrent units in time order.

Figure 4:
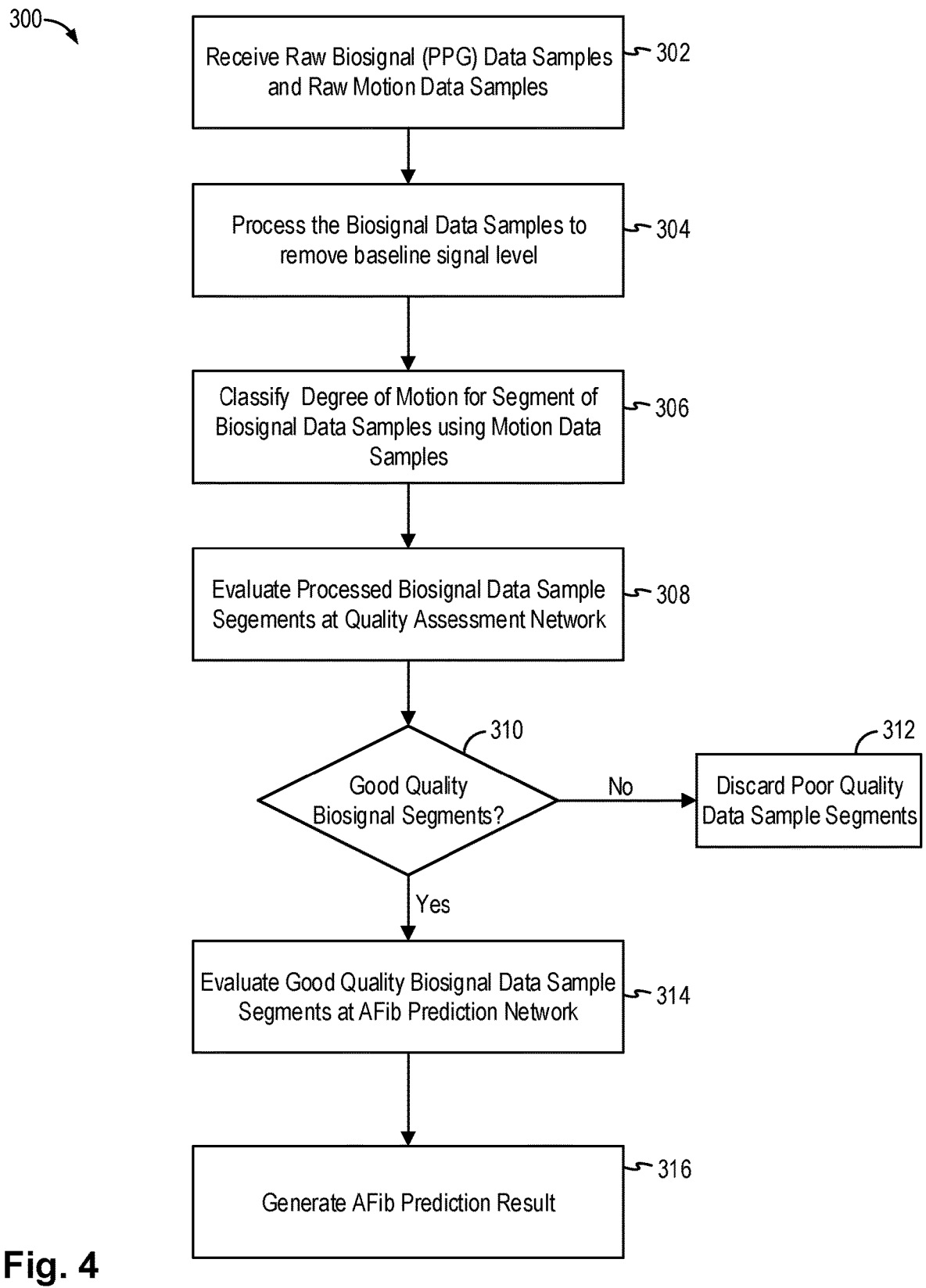
FIG. 4 is a flowchart illustrating a method for AFib detection in a user wearable device in embodiments of the present invention.

FIG. 4 is a flowchart illustrating a method for AFib detection in a user wearable device in embodiments of the present invention. In some embodiments, the method 300 can be implemented in a processor of a wearable device, such as the processor 130 of the user-wearable device 100 in FIGS. 1 and 2. Referring to FIG. 4, the method 300 starts at receiving a signal channel of biosignal data samples from a first sensor implemented in the user-wearable device (302). For example, the biosignal data samples can be a PPG data samples. The method 300 also receives a single channel of motion data samples from a second sensor implemented in the user-wearable device (302). For example, the motion data samples can be accelerometer data samples. In the present embodiment, the method 300 receives raw data samples, that is, data samples that have not been processed or have been minimally processed.

At 304, the method 300 performs baseline signal level removal on segments of the biosignal data samples to provide processed biosignal data sample segments. At 306, the method 300 classifies a degree of motion associated with each segment of the biosignal data samples using the motion data samples collected contemporaneously with the biosignal data samples. In one embodiment, the degree of motion is classified into a first motion indicator indicating moderate motion and a second motion indicator indicating vigorous motion. In some embodiment, the method 300 classifies the degree of motion associated with each segment of the biosignal data samples based on an average of magnitudes in three axes of the motion signal sensed by the accelerometer.

The method 300 continues at 308 where the processed biosignal data sample segments and the corresponding motion indicators for the respective segments are provided to a quality assessment network which implements a first deep learning model that was previously trained based on a set of quality labels and one or more sets of quality training data. At 310, the method 300 generates a signal quality indicator identifying each processed biosignal data sample segment as having good signal quality or poor signal quality. Poor quality biosignal data sample segments are discarded (312).

The method 300 continues at 314 where processed biosignal data sample segments having associated signal quality indicator designating good signal quality are provided to a AFib prediction network which implements a second deep learning model that was previously trained based on AFib annotations and one or more sets of AFib detection training data. At 316, the method 300 generates a prediction result being indicative of a probability that atrial fibrillation is present in a given segment of the biosignal data samples. In some embodiments, in response to detecting that AFib is present, the AFib detection method 300 sends a notification to the user. For example, the notification may be sent via an application on a mobile device and/or the wearable device.

In an alternate embodiment, the method 300 provides the processed biosignal data sample segments having associated signal quality indicator designating good signal quality and the associated motion indicators for the respective segments to the second deep learning model.

Figure 5:
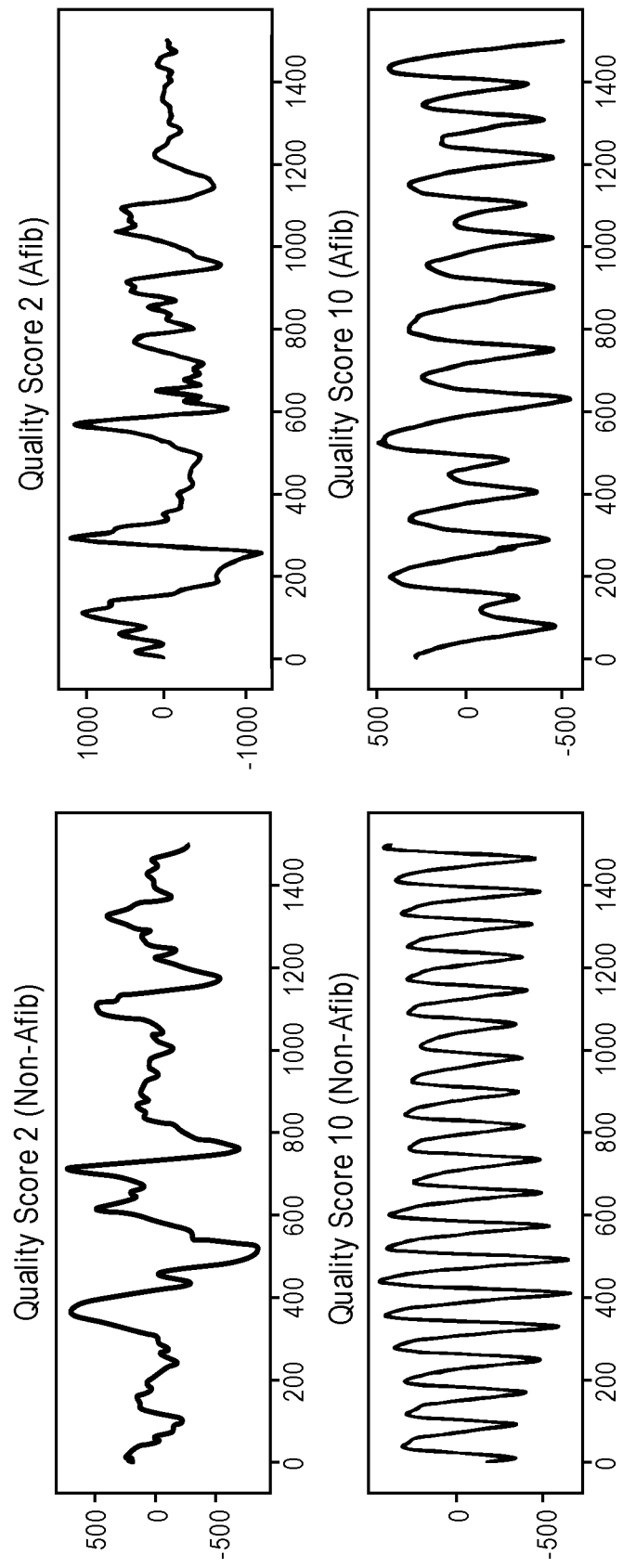
FIG. 5 illustrates examples of different PPG data sample segments annotated with different quality scores as the quality labels.

In embodiments of the present invention, the quality assessment network or module applies the first deep learning model to evaluate the PPG data samples to determine a good or poor signal quality level. The first deep learning model was previously trained based on a set of quality labels. In one example, a set of PPG data is collected, and the signal quality of the collected PPG data is assessed by human expert and a quality index from 1 (lowest quality) to 10 (highest quality) can be assigned to each segment as the quality label. For example, the quality of signal is assessed based on morphology, periodicity, presence of dicrotic notch and consistency of beats. FIG. 5 illustrates examples of different PPG data sample segments annotated with different quality scores as the quality labels. Referring to FIG. 5, signal segments from the left column are labeled as non-AFib and those from the right column are labeled as AFib. When quality of signals is low, it is impossible to distinguish AFib signals from those are not AFib.

As used herein, the term "deep learning model" refers to classification models that may require extended training times in exchange for more accurate classifications. In practice, the training of a classification model is carried out on high power computers and the trained model is then deployed on the device where inference using the model is performed. In some embodiments, deep learning neural network models, as described herein, may be considered a deep learning model. However, other machine learning and/or classification techniques may be employed to generate deep learning model. Briefly stated, embodiments of the present invention are directed towards AFib detection or event prediction using machine learning that may be incrementally refined based on expert input. In at least one of the various embodiments, data may be provided to a deep learning model that has been trained using a plurality of classifiers (index, labels or annotations) and one or more sets of training data and/or testing data.

The detail construction of the AFib detection system of the present invention will now be described with reference to one embodiment using PPG sensor as the biophysiological sensor. The embodiments described below are illustrative only and not intended to be limiting.

In one exemplary embodiment, PPG data is collected from 19 patients with 1443 PPG segments collected by a wearable device. Each PPG segment contained 30 seconds of data with a sampling rate of 100 Hz resulting in 3000 samples per segment. In addition, each PPG segment has accelerometer readings recorded simultaneously at 100 Hz. Among all the PPG samples, 1101 of them have AFib and 342 have other rhythms. A quality index range from 1 (lowest quality) to 10 (highest quality) manually annotated by human experts also comes along with each PPG sample. The quality of signal may be assessed based on factors including periodicity, presence of dicrotic notch and consistency of beats. FIG. 5 illustrates exemplary waveforms of PPG signals. ECG samples were also collected and annotated for presence of AFib episode. Such annotations are used as ground truth for AFib.

Data Processing

In one embodiment, the AFib detection system applies wavelet decomposition with 8 levels and Daubechies wavelet on each segment of PPG and approximation channel is removed in wavelet reconstruction to remove the baseline. A set of motion significance measures are calculated for each segment based on corresponding magnitude of the accelerometer signal to capture the degree of motion during the recording of the PPG signal. For example, the motion significance measures can be calculated as average of magnitudes in three axes: $Acc=\sqrt{x^2+y^2+yz^2}$ of accelerometer signal. Specifically, each motion segment contains results in two motion indicators, motion moderate and motion vigorous, which are calculated by thresholding the percentage of standard deviations on half-second window over 30-second PPG segment. The thresholds may be predetermined. Furthermore, the AFib detection system groups the signal segments having quality index higher than 6 to be good quality segments (labeled as 0) and the rest as poor quality segments (labeled as 1), resulting in 716 good quality segments and 727 bad quality segments, for example.

Figure 6:
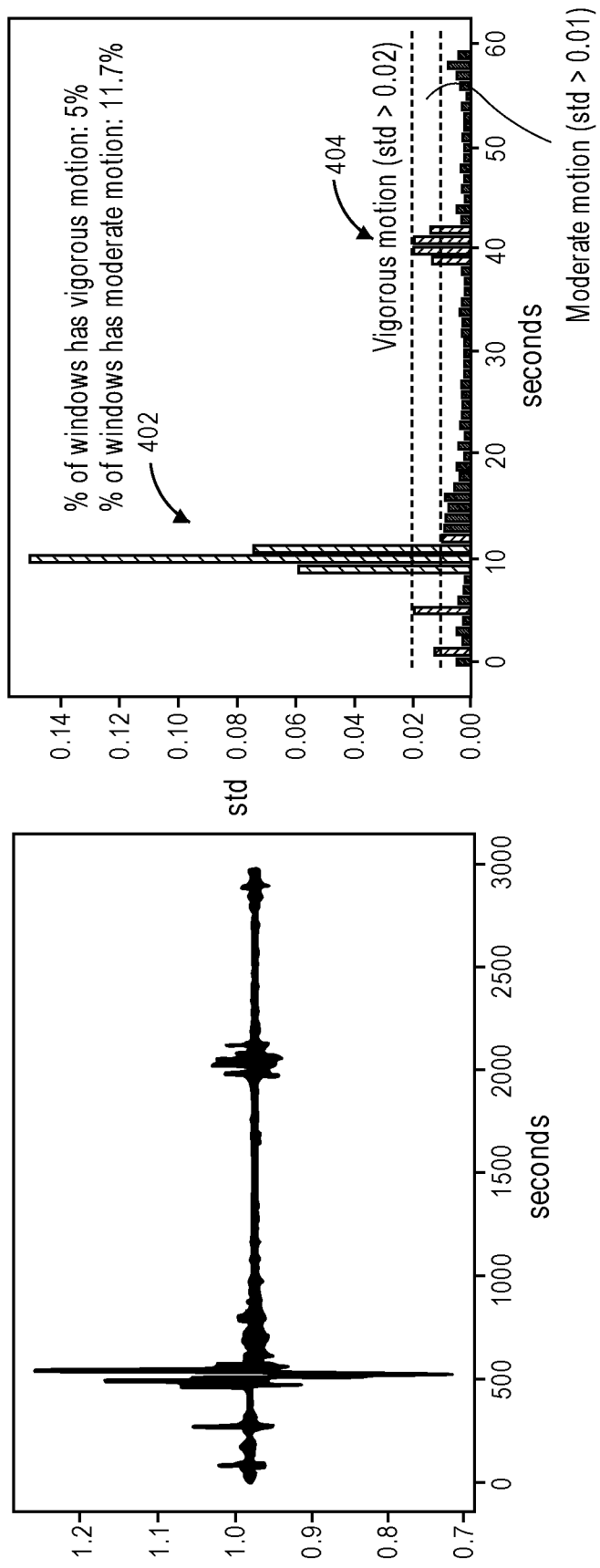
FIG. 6 illustrates exemplary waveforms of motion significance measure on a 30-second segment of PPG signal.

FIG. 6 illustrates exemplary waveforms of motion significance measure on a 30-second segment of PPG signal. The left waveform illustrates a raw accelerometer signal. The right waveform illustrates 0.5 second windows that have vigorous motion (402) and moderate motion (404). The percentages of windows in vigorous and moderate motion (showing on the top) are used as motion significance measures described above.

Quality Assessment Network

Figure 7:
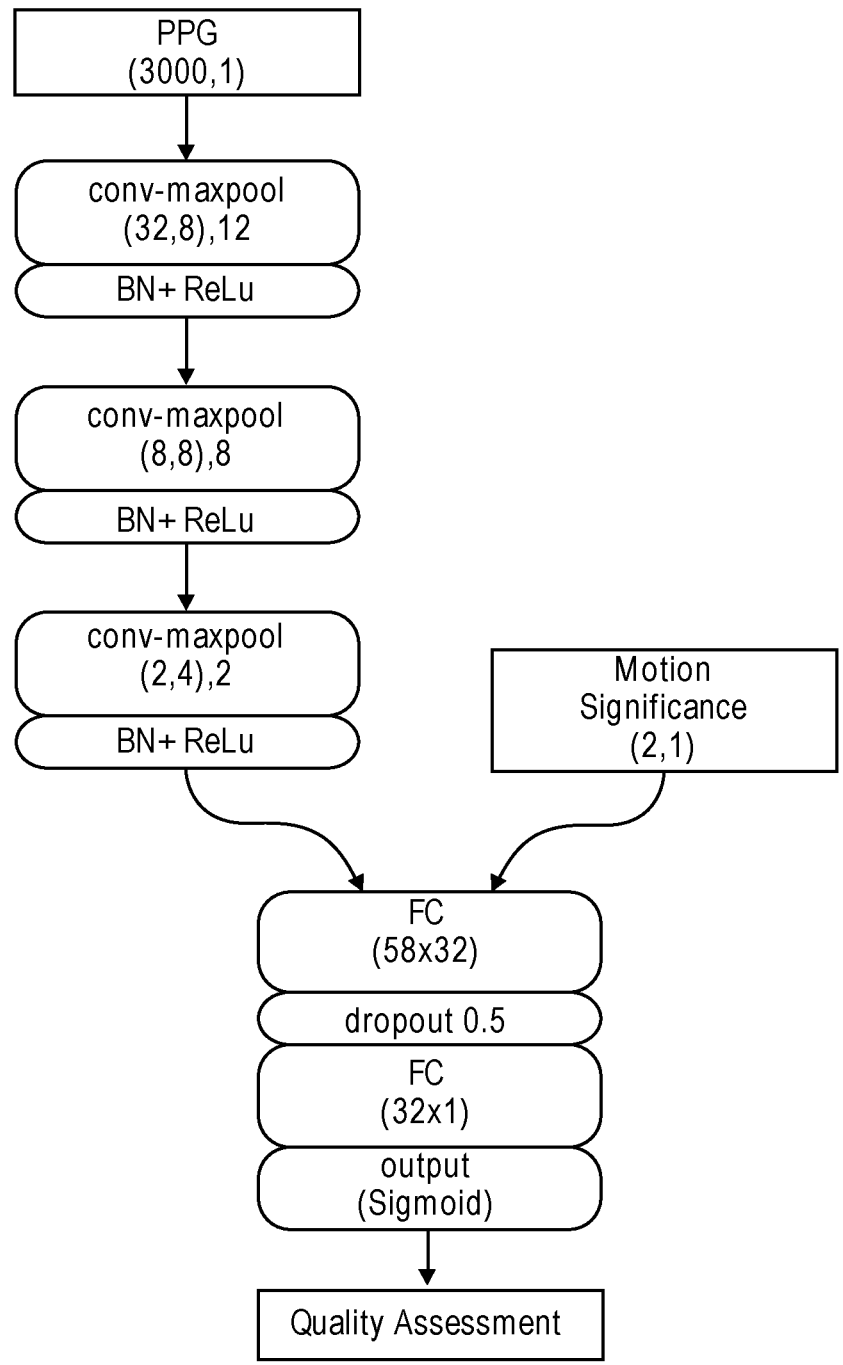
FIG. 7 illustrates the architecture of the quality assessment network in some embodiments.

FIG. 7 illustrates the architecture of the quality assessment network in some embodiments. Referring to FIG. 7, the quality assessment network includes a multimodal neural network is designed which accepts two inputs, the preprocessed PPG signal with length of 30 seconds and the vigorous motion measure mentioned above, and predicts the probability of a signal being good quality or not. The motion variable is injected at the last stage along with learned features of PPG from convolutional layers. The model is trained by binary good-poor quality labels described above.

The Quality Assessment Network shown in FIG. 7 consists of three convolutional layers with max-pooling, batch-normalization and rectified linear unit (ReLU) as activation function, followed by one fully-connected layer and one output layer. There are 8, 8 and 4 filters with sizes of 32, 8 and 2 along the temporal dimension in first, second and third layer. The pooling size of 1D max pooling layers are 12, 8 and 2 respectively. The samples are not padded for filters. The output from convolutional layers are flattened and concatenated with the motion significance measure for that signal and is fed into one fully connected layer with ReLU activation, followed by the output layer with a sigmoid activation function which outputs the probability of segment having poor-quality.

The model is regularized to prevent overfitting. With L2 constraint imposed on the weights of all convolutional filters and a drop-out regularization on the fully connected layer. The parameter for L2 constraint is 0.05 and rate for dropout is 50%. Total number of parameters of this model is 2,529.

AFib Prediction Network

In embodiments of the present invention, the AFib prediction network includes a second neural network which accepts the preprocessed PPG signal that is predicted as good signal by the quality assessment network. The model is trained with AFib annotation on corresponding 30-second ECG signal as ground truth targets, according to one embodiment. To effectively extract both local structures of waveforms and their temporal progression as features for predicting AFib, a CRNN model (Convolution-Recurrent Hybrid Model) is developed which is a hybrid model of CNN and recurrent neural network (RNN). The AFib prediction network may also be implemented using a CNN model without recurrent structures as a baseline, or other types of deep neural network architectures.

In one embodiment, the CNN baseline model is a 3-layer CNN similar to the quality assessment network (see FIG. 6). The difference is in number of filters in each convolution layer, where this model has 32, 16 and 16 filters. In particular, more filters are needed to extract intricate waveform structures that are invariant in AFib PPG segments. In addition, in the present embodiment, there is no motion measure concatenated as a second input. The total number of parameters of this model is 13,121. In other embodiments, the motion measure may be concatenated as a second input to the CNN baseline model.

Figure 8:
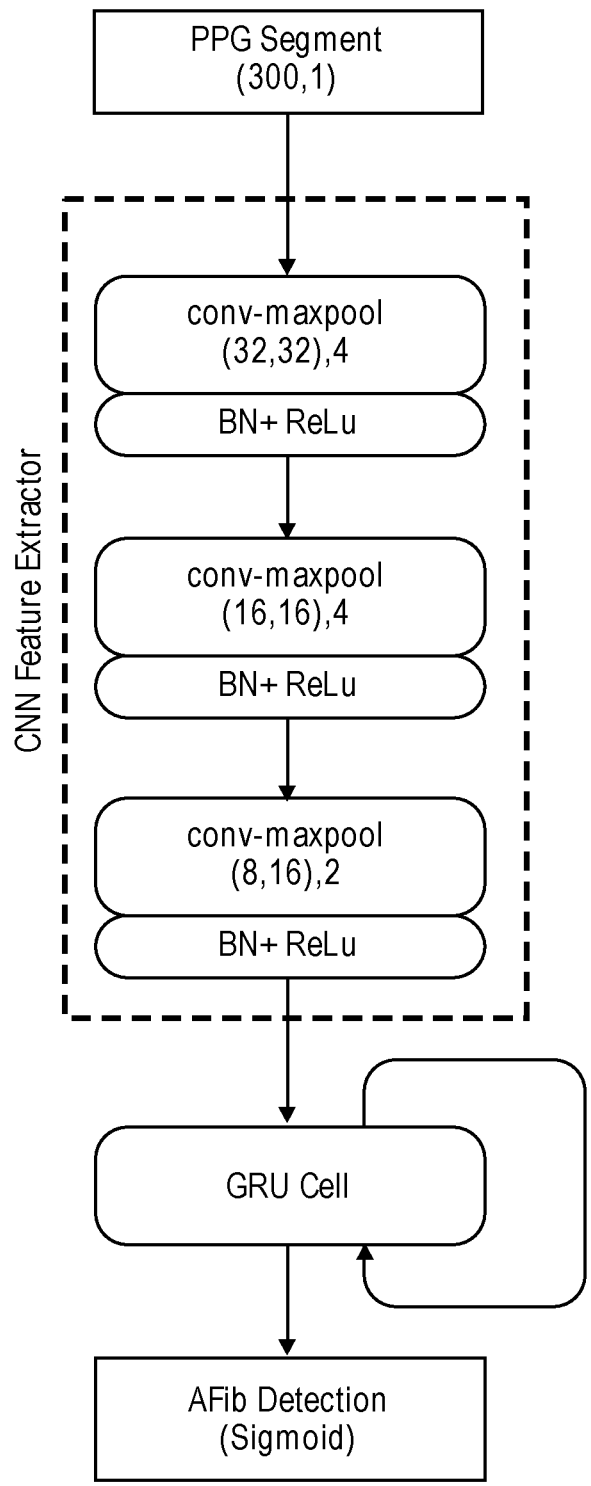
FIG. 8 illustrates the architecture of the AFib Prediction Network using the CRNN model in some embodiments.

FIG. 8 illustrates the architecture of the AFib Prediction Network using the CRNN model in some embodiments. Referring to FIG. 8, the CRNN model includes an RNN structure with signals from consecutive time windows as input to better model the complex time dependencies of PPG signal, such as irregular patterns between fixed time segments. In the CRNN model, the 30-second segment of data samples are split into 10 three-second-window segments and each segment is fed into a CNN feature exac GRU cells in time order.

To efficiently extract waveform structures from each time window, a feature extractor containing three convolutional layers to each window is applied. The number of filters are 32, 16 and 16 at the first, second and third layer of CNN. The size of filters along the temporal dimension are 32, 16 and 8 and the size of 1D max pooling layer are 4, 4, and 2 at each level, respectively. The samples are not padded for filters. Weights of filters in CNN are shared among all temporal steps, with the premise that features regarding waveform structures are invariant along time dimension. Rectified Linea Unites (ReLU) is used for activation function for all convolutional layers. The extracted representations of each window are then fed into Gated Recurrent Units (GRU), at each temporal step (3 seconds). The size of hidden layer in each GRU cell is 16. Dropout (50%) is applied on the hidden layer of the recurrent units, as shown in FIG. 8.

Optimization

The weights of each model were optimized by Adam optimizer (learning rate of 0.0005) via back-propagation, using binary cross entropy as loss function. To address the imbalanced class sizes in AFib detection tasks, a higher class weight is attributed to the underrepresented class (segments without AFib) of 0.7 and the other class 0.3 when training AFib detection models. The models can be trained with mini-batches of 64 examples. Training is stopped at 150 epochs or whenever the validation error stops improving for 10 consecutive iterations to prevent overfitting.

Quality Assessment Results

The present system may utilize a five-fold cross validation to assess the performance of the deep learning models. The present system may use mean accuracy of the test set in each fold (ACC) and a pooled AUC using predicted probabilities of the test set in each fold. To demonstrate the effectiveness of the model, a simple rule-based baseline model may be incorporated, in which the threshold of motion measures is set to separate signals from good and poor quality. According to one embodiment, the present system further tests two alternative models: a CNN model without adding motion measures as input and one CNN model using both raw accelerometer signal and PPG signal. The evaluations are tested against human assessment as ground truth. The deep learning model for quality assessment used herein has much higher accuracy and AUC than the baseline model achieving AUC of 95.21%.

AFib Detection Results

In order to evaluate the AFib detection system independently, all signals that are labeled to be good quality (with quality score >6) are used to train and validate the AFib prediction models. The resulting samples of signals are dominated by AFib samples. In order to train more robust models, a higher weight is attributed to the underrepresented class in loss functions of the models.

Two models are tested, including above mentioned two architectures: CNN and CRNN. Both models have accuracy higher than 97% and AUC higher than 99%. The hybrid model achieved best performance overall, showing that modeling time-dependency information is helpful for predicting AFib. The result shows that a relatively small network structure with number of parameters in range of 10,000 can achieve very high performance.

In embodiments of the present invention, the deep learning AFib detection system using PPG signal showed very high performance, with minimum manual feature engineering. By training a quality assessment network, the system is capable of accurately filtering out bad signals and thus ensures robust prediction by the AFib detection algorithm. This will be very effective when signals come from a wearable device and are subject to large variation in quality. Moreover, even a small convolutional network can predict AFib with high accuracy.

Aspects of this disclosure are described herein with reference to flowchart illustrations or block diagrams, in which each block or any combination of blocks may be implemented by computer program instructions. The instructions may be provided to a processor of a general purpose computer, special purpose computer, or other programmable data processing apparatus to effectuate a machine or article of manufacture, and when executed by the processor the instructions create means for implementing the functions, acts or events specified in each block or combination of blocks in the diagrams.

In this regard, each block in the flowchart or block diagrams may correspond to a module, segment, or portion of code that including one or more executable instructions for implementing the specified logical function(s). It should also be noted that, in some alternative implementations, the functionality associated with any block may occur out of the order noted in the figures. For example, two blocks shown in succession may, in fact, be executed substantially concurrently, or blocks may sometimes be executed in reverse order.

A person of ordinary skill in the art will appreciate that aspects of this disclosure may be embodied as a device, system, method or computer program product. Accordingly, aspects of this disclosure, generally referred to herein as circuits, modules, components or systems, may be embodied in hardware, in software (including firmware, resident software, micro-code, etc.), or in any combination of software and hardware, including computer program products embodied in a computer-readable medium having computer-readable program code embodied thereon The above detailed descriptions are provided to illustrate specific embodiments of the present invention and are not intended to be limiting. Numerous modifications and variations within the scope of the present invention are possible. The present invention is defined by the appended claims.

What is claimed is:

1. An apparatus, comprising:
   a sensor module comprising a first sensor measuring a biological signal and a second sensor measuring a motion signal, the sensor module providing biosignal data samples and motion data samples as output;
   a data processing module processing segments of the biosignal data samples, each segment including biosignal data samples collected over a predetermined time duration, the data processing module removing a signal baseline from each segment of biosignal data samples and to generate processed biosignal data sample segments; and the data processing module further generating a motion significance measure for each segment of biosignal data samples using the motion data samples collected contemporaneously with the biosignal data samples, the motion significance measure being indicative of a degree of motion during the sensing of the respective segment of biosignal data samples;
   a quality assessment module generating a signal quality indicator based on the processed biosignal data sample segments and the corresponding motion significance measure using a first deep learning model, wherein the first deep learning model comprises a multimodal neural network including a plurality of convolutional layers and a fully-connected layer, and the processed biosignal data sample segments are fed to the plurality of convolutional layers, and the corresponding motion significance measure is fed to the fully-connected layer independently from the processed biosignal data sample segments; and
   an event prediction module determining, depending on the signal quality indicator generated by the quality assessment module, to discard the processed biosignal data sample segments or proceed to generate an event prediction result based on the processed biosignal data sample segments using a second deep learning model.

2. The apparatus of claim 1, wherein the biological signal of the user comprises a cardio-related physiological signal and the motion signal comprises an inertial measurement signal.

3. The apparatus of claim 1, wherein the motion significance measure comprising a motion indicator indicating moderate motion or vigorous motion based on a standard deviation on a window of the motion data samples.

4. The apparatus of claim 1, wherein the apparatus comprises a user-wearable device, the first sensor comprises a photoplethysmography (PPG) sensor and the second sensor comprises an accelerometer.

5. The apparatus of claim 4, wherein the biosignal data samples comprises raw PPG data samples and the motion data samples comprises raw accelerometer data samples.

6. The apparatus of claim 4, wherein the data processing module generates the motion significance measure for each segment of motion data samples based on an average of magnitudes in three axes of the motion signal sensed by the accelerometer.

7. The apparatus of claim 1, wherein the event prediction module evaluates the processed biosignal data sample segments with the associated motion significance measure using the second deep learning model.

8. The apparatus of claim 1, wherein each of the plurality of convolutional layers has max-pooling, batch normalization and rectified linear unit as activation function, wherein the outputs from the convolutional layers are flattened and concatenated with the corresponding motion significance measure and fed into the fully connected layer.

9. The apparatus of claim 1, wherein the second deep learning model comprises a hybrid model of convolutional neural network (CNN) and recurrent neural network (RNN), wherein each segment of the processed biosignal data sample segments is split into a plurality of sub-segments where each sub-segment is fed into gated recurrent units in a time order.

10. The apparatus of claim 1, wherein in response to the event prediction result indicating a high probability that an event is present in a given segment of the biosignal data samples, the user-wearable device provides a notification to the user.

11. The apparatus of claim 1, wherein the sensor module provides a first channel of biosignal data samples and a second channel of motion data samples.

12. The apparatus of claim 1, wherein the quality assessment module evaluates each segment of the processed biosignal data sample segments with the motion significance measure using the first deep learning model that was previously trained based on a plurality of quality labels and one or more sets of quality training data, the signal quality indicator identifying the each segment of the processed biosignal data sample segments as having good signal quality suitable for proceeding to generate the event prediction result or poor signal quality unsuitable for proceeding to generate the event prediction result.

13. The apparatus of claim 12, wherein the event prediction module receives the processed biosignal data sample segments with the associated quality indicator designating good signal quality and to evaluate the processed biosignal data sample segments using the second deep learning model that was previously trained based on event annotations and one or more sets of event detection training data, the event prediction module generating the event prediction result as output, the event prediction result being indicative of a probability that an event is present in a given segment of the biosignal data samples.

14. The apparatus of claim 13, wherein the event prediction module comprises an AFib prediction module configure to generate an atrial fibrillation (AFib) prediction result being indicative of a probability that atrial fibrillation is present in a given segment of the biosignal data samples, the AFib prediction module evaluating the processed biosignal data sample segments using the second deep learning model wherein the second deep learning model was previously trained based on AFib annotations and one or more sets of AFib detection training data.

* * * * *